United States Patent

Hart et al.

Patent Number: 5,618,297
Date of Patent: Apr. 8, 1997

[54] OBTURATOR WITH INTERNAL TIP PROTECTOR

[75] Inventors: Charles C. Hart, Huntington Beach; Vincent C. Tangherlini, Rancho Santa Margarita; Nabil Hilal, Mission Viejo, all of Calif.

[73] Assignee: Applied Medical Resources, Laguna Hills, Calif.

[21] Appl. No.: 322,698

[22] Filed: Oct. 13, 1994

[51] Int. Cl.⁶ .................................................. A61M 5/00
[52] U.S. Cl. ........................... 606/185; 604/164; 604/264
[58] Field of Search .................................... 604/164, 264, 604/272; 606/167, 181, 182, 183, 184, 185; 30/340, 342, 366, 60, 162, 71

[56] References Cited

U.S. PATENT DOCUMENTS

| | | | |
|---|---|---|---|
| 4,523,379 | 6/1985 | Osterhout et al. | 30/151 |
| 4,601,710 | 7/1986 | Moll | 604/165 |
| 5,275,583 | 1/1994 | Crainich | 604/264 |
| 5,388,589 | 2/1995 | Davis | 128/754 |
| 5,423,843 | 6/1995 | Werner | 606/167 |

FOREIGN PATENT DOCUMENTS 2697150  4/1994  France.

*Primary Examiner*—Michael Buiz
*Assistant Examiner*—Patrick W. Rasche
*Attorney, Agent, or Firm*—Richard L. Myers

[57] ABSTRACT

An obturator adapted for use in penetrating a body wall of a patient includes an elongate shaft having an axis extending between a proximal end and a distal end. A handle is disposed at the proximal end and an arcuate cutting edge is formed at the distal end of the shaft. The shaft may include a plurality of inner walls and passages, with a shield mechanism movable within the passages from a retracted cutting position to an advanced position. A system of flanges and walls can be used to maintain the shield elements in close proximity to and sliding engagement with the associated inner walls. In an associated method of manufacture, the shaft of the obturator can be extruded.

13 Claims, 6 Drawing Sheets

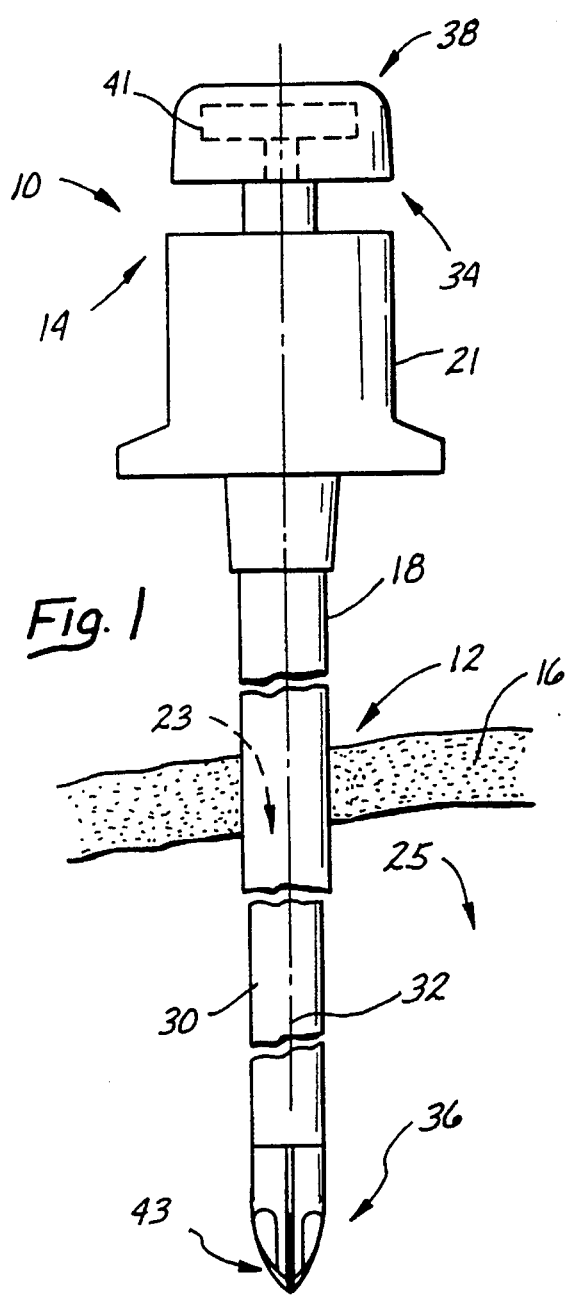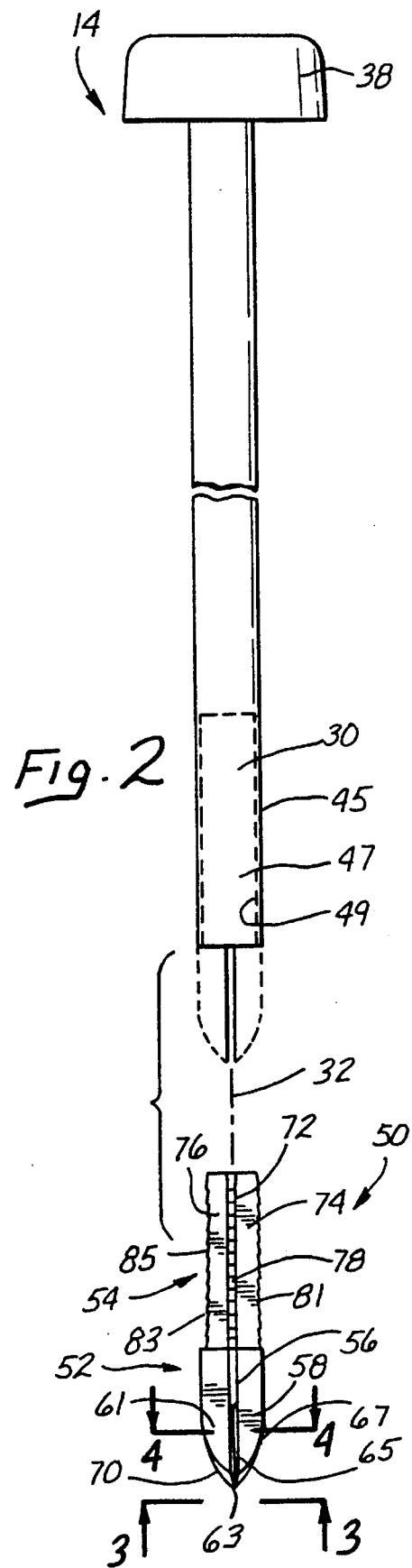

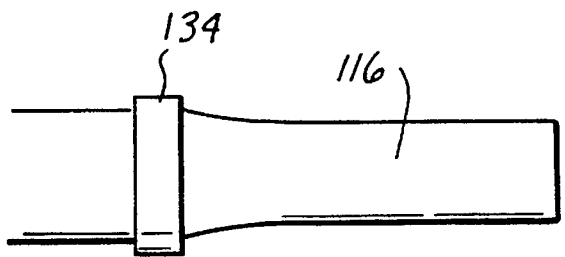
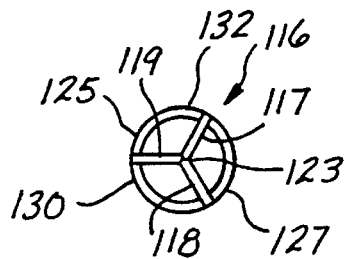
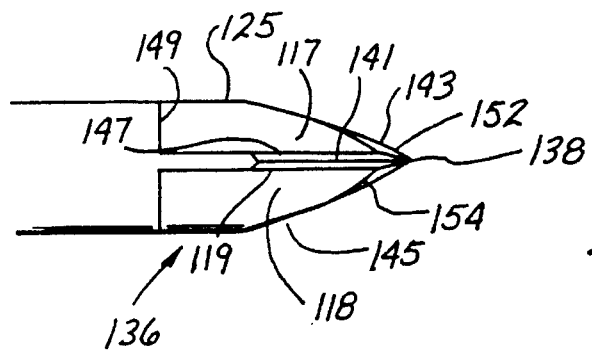
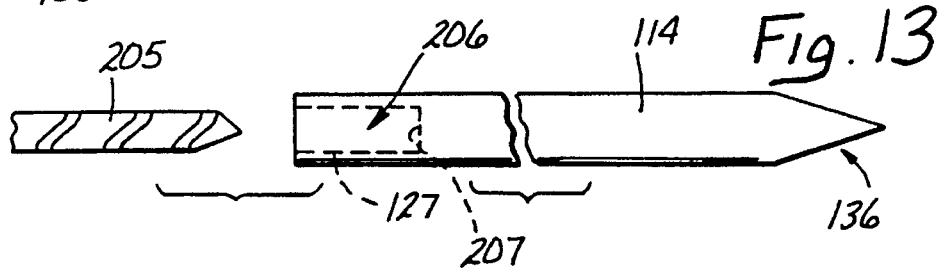
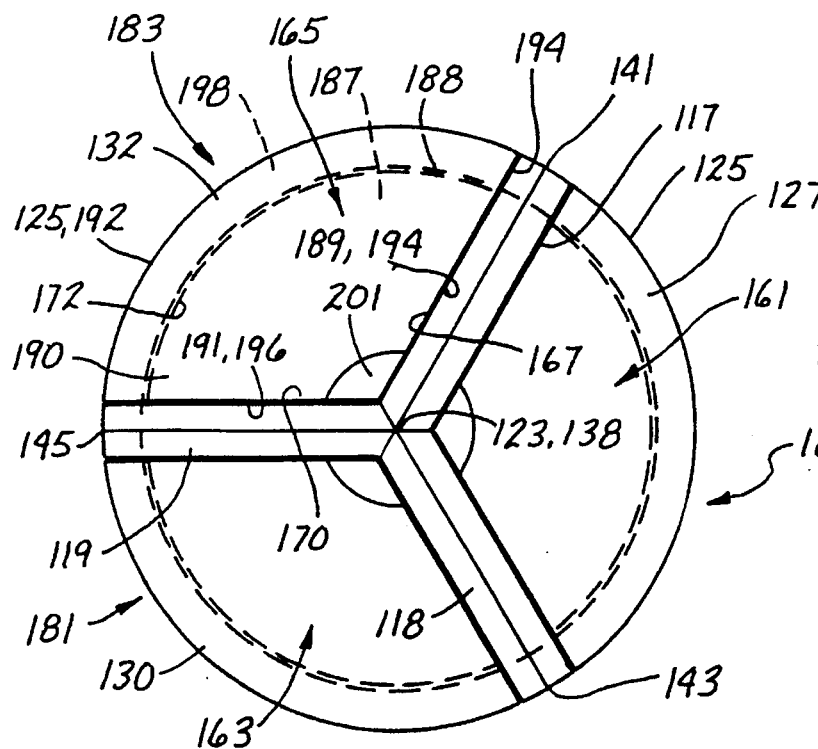

OBTURATOR WITH INTERNAL TIP PROTECTOR

BACKGROUND OF THE INVENTION

1. Field of the Invention

This invention relates generally to surgical access devices and more specifically to trocars and associated obturators which provide operative access across a body wall of a patient.

2. Discussion of the Prior Art

A trocar is a surgical instrument which is used to provide access across a body wall and into a body cavity, such as the abdominal cavity, in order to facilitate use of surgical instruments in the body cavity. The trocar consists of a hollow cannula which is operatively positioned across the body wall using an obturator. The obturator is removably positioned within the cannula and has a sharpened distal tip which is used to penetrate the body wall. While the sharpened tip of the obturator has facilitated penetration of the body wall, shields have been required to isolate this tip from internal organs which may be present on the other side of the body wall.

Shields of the prior art have taken many different forms. In one case, the shields have been formed as external sleeves advanceable to cover the sharp tip upon penetration of the body wall. In other cases the sharp tip has been shielded by retracting the obturator into the cannula. The shielding function has also been accomplished by forming the sharp tip as a plurality of blades and then providing shields in the form of internal rods disposed between the blades. Representative of this art is U.S. Pat. No. 5,275,583 issued on Jan. 4, 1994 to Lawrence Crainich and entitled Trocar Assembly with Independently Acting Shield Means.

In accordance with the prior art, the sharpened tip of the obturator has been formed from a hollow shaft or a plurality of individual blades. With the shaft configuration, the distal end has been ground to form multiple facets each extending from an axial point proximally and outwardly. The facets of the past have been formed with a planar configuration so that adjacent facets have formed a straight cutting edge where they intersect. Three facets have typically been equally spaced around the 360° distal tip.

A cutting edge has been formed at the intersection of each adjacent pair of the facets. The angle at the sharp cutting edge is equal to the angle between the adjacent facets; one-half of this angle is commonly referred to as the facet angle. In the past, the cutting edges have been formed at an angle not less than the facet angle which in a three-facet embodiment is 60°.

Obturators of the blade configuration have been sharpened in a similar manner so that the cutting edges of these blades have also been ground to a facet angle of about 60°. In order to facilitate penetration of the body wall and reduce trauma to the patient, it is desirable to make these cutting edges as sharp as possible.

As noted, it is also desirable to shield the sharpened tip immediately upon penetration of the body wall. Shields of the past have been provided to move from a relatively retracted position to a relatively advanced position in order to cover the sharp tip. Typically the retracted position has required that the shield be displaced from the tip the full length of the facets. Then, in order to cover the distal tip, the shield has been required to move over the full length of the facet. Where this distance has been particularly long, considerable time has been required to fully shield the sharp tip.

SUMMARY OF THE INVENTION

These deficiencies of the prior art are overcome in accordance with the present invention which includes an obturator shaft with a sharpened distal tip. This tip is formed with arcuate cutting edges which facilitate insertion of the obturator and cannula through the body wall. The arcuate configuration is formed in a convex configuration which more closely matches the forces which resist penetration at various positions along the axis of the obturator.

The cutting edges are sharpened by a bevel which forms an angle with the cutting edge which is less than a facet angle. This greatly enhances the sharpness of the cutting edge and facilitates penetration of the body wall.

Shielding of the sharp tip is accomplished by a plurality of rods each of which extends between an associated pair of the blades. These rods are moved from a retracted position to an advanced position over a distance which is equivalent to the axial length of the bevel rather than the axial length of the facets. This greatly reduces the distance which the shielding rods must travel to accomplish full shielding of the sharp tip. With the reduced distance, the time for complete shielding is also greatly reduced.

In one form of the invention, the obturator shaft is provided in the form of a plastic tube having an inner surface. A metal cutting tip of the obturator is formed with a distal cutting section and a proximal mounting section. This mounting section includes mounting members which extend to an outer edge that is serrated. This configuration of the cutting tip facilitates a fixed frictional relationship between the mounting section and the inner surface of the tube at the distal end of the shaft.

In one aspect of the invention, the obturator includes an elongate tube having a wall with an outer surface, an inner surface and an axis extending between a proximal end and a distal end. A handle is disposed at the proximal end and a cutting tip is disposed along the axis in a fixed relationship with the elongate tube at the distal end of the tube. The cutting tip includes a cutting section and a mounting section having at least two mounting members extending outwardly of the axis of the tube to frictionally engage the inner surface of the tube. The mounting members can be provided with an outer edge which is serrated in order to enhance the frictional relationship with a tube.

In an additional aspect of the invention, the elongate shaft has an outer wall with an outer surface and an inner surface. A tip section is disposed at the distal end of the elongate shaft and includes a plurality of inner walls which are angularly spaced around the axis of the shaft. The inner walls of the tip section extend to engage outer walls of the shaft and to form with the outer walls a plurality of lumens extending at least partially along the shaft. At least one of the inner walls is defined by an inclined edge extending along a line from the axis of the shaft to the outer surface of the shaft. A sharpening bevel extends along the inclined edge and has a radial length and an axial length. At least one shield is disposed in an associated one of the lumens of the shaft. The shield includes portions disposed in juxtaposition to at least one of the inner walls, the portions extending radially outwardly to the outer surface of the shaft. The shield extends axially from the associated lumen between a retracted position wherein the sharpened edge is exposed to facilitate cutting of the wall, and an extended position wherein the sharpened edge is proximate of the shield to inhibit cutting of the body wall. These extended and retracted positions are separated by an axial distance not greater than the axial length of the bevel.

In a further aspect of the invention the cutting tip is disposed at the distal end of the shaft and includes a first cutting edge and a second cutting edge which extend from a distal tip proximally outwardly of the axis of the shaft. A first imaginary plane extends between the axis of the shaft and the first cutting edge while a second imaginary plane extends through at least a first point on the first cutting edge and a second point on the second cutting edge. This second imaginary plane is parallel to the first cutting edge at both the first point and the second point and forms a facet angle with the first imaginary plane. A bevel disposed along the first cutting edge forms a bevel angle with the first imaginary plane which is less than the facet angle between the first and second imaginary planes. This provides a sharper cutting edge which further facilitates penetration of the body wall by the obturator. In a preferred embodiment, the first cutting edge has the configuration of an arc and the second imaginary plane is tangential to the arc at the first point.

An additional aspect of the invention includes a process for making an obturator. This process includes the steps of providing a shaft having an outer surface and an axis extending between a proximal end and a distal end. The shaft includes a plurality of inner walls angularly spaced around the axis and extending outwardly from the axis to the outer surface. The shaft also includes a plurality of outer walls each extending between an associated pair of the inner walls and defining with the inner walls the outer surface of the shaft. In accordance with the process, the outer walls of the shaft are removed at the distal end of the shaft to expose the inner walls. An inclined edge is then formed along at least one of the exposed inner walls to extend from the outer surface to a point at the distal end of the shaft. Sharpening this inclined edge facilitates penetration of tissue by the obturator. In the preferred process, the inner walls and outer walls of the shaft are formed in an integral configuration by extruding the shaft.

These and other features and advantages of the invention will be more apparent with the description of preferred embodiments and reference to the associated drawings.

DESCRIPTION OF THE DRAWINGS

FIG. 1 is a side elevation view of a trocar including an obturator penetrating a body wall;

FIG. 2 is an exploded side elevation view of one embodiment of the obturator including a tubular shaft and a distal tip having mounting elements with serrated edges;

FIGS. 5–11 illustrate a method for manufacturing a further embodiment of the invention;

FIG. 5 is a side view illustrating extrusion of a shaft having inner walls and outer walls;

FIG. 6 is a radial cross section view of the shaft extruded in FIG. 5;

FIG. 7 is a side view of the distal tip of the shaft illustrating a step for removing the outer walls to expose the inner walls of the shaft;

FIG. 8 is an enlarged distal end view of the obturator illustrated in FIG. 7;

FIG. 9 is a perspective view of a shield associated with the present invention;

FIG. 10 similar to FIG. 8, of a further embodiment of the wall and shield structure of the present invention;

FIG. 11 is a radial cross section view similar to FIG. 10 of an additional embodiment of the wall and shield structure of the present invention;

FIG. 13 is a side elevation view illustrating the step of removing the inner walls at the proximal end of the shaft;

DESCRIPTION OF PREFERRED EMBODIMENTS AND BEST MODE OF THE INVENTION

Figure 3:
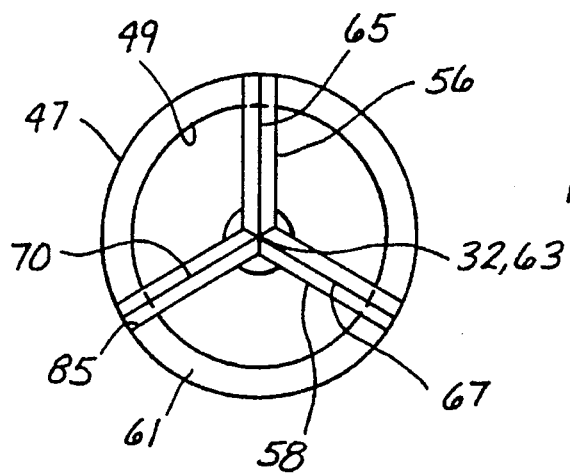
FIG. 3 is a distal end view of the obturator of FIG. 2 with the distal tip mounted in the tubular shaft.

A trocar is illustrated in FIG. 1 and designated generally by the reference numeral 10. The trocar 10, which commonly includes a cannula 12 and an obturator 14, is adapted to provide access across a body wall, such as an abdominal wall 16. This access is ultimately provided by the cannula 12 which commonly includes an elongate tube 18 and a seal housing 21. It is the tube 18 which provides access in the form of a working channel 23 across the body wall 16. Various instruments can be inserted through the working channel 23 to access a body cavity such as the abdominal cavity 25.

When the cannula 12 of the trocar 10 is operatively disposed across the body wall 16, it is important that its interior or distal end be dull so that interior organs are not susceptible to puncture or cutting. However, providing the cannula with a dull leading end, does not facilitate its preferred method of placement by puncturing the abdominal wall 16. It is for this reason that the removable obturator 14 is provided to puncture the wall 16 and thereby permit placement of the cannula 12. The obturator 14 is inserted into the cannula 12 and extends beyond the elongate tube 18 to facilitate puncture of the abdominal wall 16.

The obturator 14 includes a shaft 30 having an axis 32 which extend between a proximal end 34 and a distal end 36. A handle 38 is disposed at the proximal end 34 and forms an enclosure for a retraction mechanism 41 such as that disclosed and claimed by applicant in patent application Ser. No. 08/045,369, filed on Apr. 9, 1993 and entitled Surgical Trocar with Cutoff Circuit, which is incorporated herein by reference. The shaft 30 is sized so that it can be removably inserted into the working channel 23 of the cannula 12 with the end 36 of the obturator 14 extending beyond the distal end of the tube 18.

At the distal end 36 of the shaft 30, the obturator 14 is provided with a sharpened tip 43 which is moveable axially through the abdominal wall 16 to operatively position the tube 18 and associated working channel 23 across the abdominal wall 16. It is this obturator 14 that is of particular interest to the present invention.

A preferred embodiment of the obturator 14 is illustrated in FIG. 2 wherein the shaft 30 has a tubular configuration. In this case, the shaft 30 is formed with a cylindrical wall 45 having an outer surface 47 and an inner surface 49. The shaft 30 is preferably made from metal in order to provide it with a generally rigid configuration. A separate cutting tip 50 includes a cutting section 52 and a mounting section 54.

The cutting tip 50 can be provided in the form of multiple blades equally spaced around the axis 32. For example, in a preferred embodiment there are three blades 56, 58 and 61 which are spaced at 120° intervals around the axis 32. In the cutting section 52, the blades 56–61 are inclined from a maximum radius distally to a point 63 on the axis 32. Thus, each of the three blades 56–61 is provided with an associated cutting edge 65, 67 and 70 which extends radially inwardly distally to the point 63. These cutting edges 65–70 can be straight as taught by the prior art, or can have an arcuate configuration, as described in greater detail below, in accordance with one aspect of the present invention.

The mounting section 54 of the cutting tip 50 is configured for insertion into the distal end of the tubular shaft 30. Within the shaft 30, the mounting section 54 frictionally engages the inner surface 49 to maintain the cutting tip 50 in a fixed relationship with the shaft 30.

This fixed relationship is enhanced in a preferred embodiment by forming the mounting section 54 as a plurality of individual partitions equally angularly spaced around the axis 32. In a preferred embodiment, the mounting section 54 has three partitions 72, 74 and 76 each of which is formed as an extension of an associated one of the respective blades 56, 58 and 61. Each of the partitions 72–76 extends radially, outwardly from the axis 32 to an associated outer edge 78, 81 and 83, which extends axially in a generally parallel relationship with the inner surface 49 of the shaft 30.

The frictional relationship between the partitions 72–76 and the wall 45 of the shaft 30 can be enhanced by forming a multiplicity of serrations along the edges 78, 81, and 83. These serrations can take the form of multiple points 85 which in a preferred embodiment are directed to face distally. This orientation of the points 85 along the serrations, facilitates insertion of the cutting tip 50 into the distal end of the shaft 30, while inhibiting separation of the cutting tip 50 from the shaft 30 once the preferred fixed relationship has been achieved.

A distal end view of the cutting tip 50 mounted within the tube 30 is illustrated in FIG. 3. In this view, it will be apparent that the cutting edges 65–70 extend radially outwardly from the point 63 to the outside diameter of the surface 47 associated with the wall 45. In the illustrated embodiment, these cutting edges 65–70 are sharpened along this entire length so that cutting is accomplished to the maximum diameter of the shaft 30. Since the outside diameter of the shaft 30 is the inside diameter of the tube 18, entry forces for the trocar 10 are minimized with substantially full diameter cutting. Very little stretching or dilation of the wall 16 is required.

Figure 4:
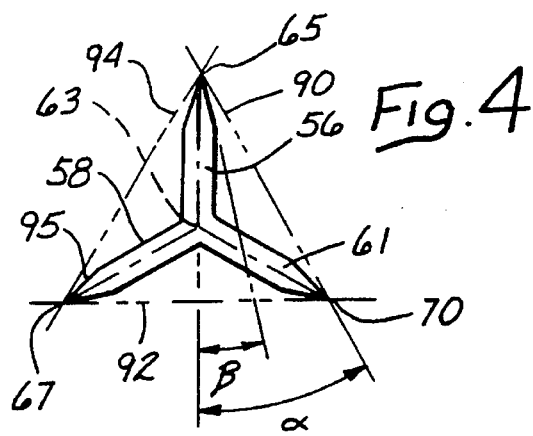
FIG. 4 is a radial cross section view of the distal tip taken along lines 4—4 of FIG. 2.

This cutting by the blades 56–61 can be enhanced in accordance with a further aspect of the invention best illustrated in FIG. 4. In the past, the inclined cutting edges 65–70 have been formed by grinding the associated blade 56–61 along three imaginary planes 90, 92 and 94, each including an adjacent pair of the cutting edges 65, 67 and 70. In the past, this grinding step not only formed the cutting edges 65–70, but also sharpened those edges to a facet angle expressed by the following Formula I:

$$\text{Facet angle} = 180\left(1 - \frac{2}{n}\right) \quad \text{(Formula I)}$$

Where:
n=the number of blades

Thus, in a three blade embodiment such as that illustrated in FIG. 4, the blades 56–61 were initially sharpened to a facet angle of 60°.

In accordance with the present invention, the blades 56–61 are sharpened to form a bevel 95 along either or both sides of the respective cutting edges 65–70. The angle between the bevel 95 and the plane of the associated blade 56–61 is referred to herein as the bevel angle and is generally less than the facet angle of Formula I. This provides a sharper cutting edge which thereby promotes cutting and reduces the force of entry for the obturator 14. In FIG. 4, the facet angle is designated $\alpha$ while the sharpened bevel angle is designated $\beta$.

The configuration of the obturator shaft 30 is of particular interest in a further embodiment of the invention. This embodiment is perhaps best illustrated in the cross-sectional view of FIG. 6. In this case, a shaft 116 includes a plurality of inner walls 117, 118 and 119 which extend radially outwardly from an axis 123 to an outer surface 125. A plurality of outer walls 127, 130 and 132 connect adjacent pairs of the inner walls 117, 118 and 119 and further define the outer surface 125 which is cylindrical in a preferred embodiment.

This construction of the shaft 116 can be formed in accordance with several processes. In a preferred method of manufacture, the shaft 116 is extruded through a die 134 as illustrated in FIG. 5. The shaft 116 can also be formed in accordance with a plastic or metal injection molding process.

The shaft configuration illustrated in FIG. 6 is of interest because it can be formed with the inner walls 117–119 integral with the outer walls 127–132. In addition, an integral tip 136 can be formed on the shaft 116 as best illustrated in FIG. 7. In this case, the tip 136 is formed by grinding the end of the shaft 116 along three planar facets. Each of the planar facets includes two of the cutting edges each of which extends along an associated one of the inner walls 117–119 from the outer surface 125 to a distal point 138. In FIG. 7, these cutting edges are designated by the reference numerals 141, 143 and 145. The cutting edges 141–145 are formed along the respective inner walls 117–119 as the distal end of the shaft 116 is ground along the planar facets to form the tip 136.

In effect, the grinding of the shaft 116 removes the outer walls 127–132 at the distal tip 136 to expose the inner walls 117–119. This exposure of the inner walls 117–119 makes it possible to further sharpen the cutting edges 141–145 for example by grinding at least one bevel along each of the cutting edges 141–145.

As illustrated in FIG. 7, the inner wall 119 can be ground to form a bevel 147 along the cutting edge 141. Similar bevels 152 and 154 can be formed along the respective cutting edges 143 and 145. Importantly, the cutting edges 141–145 are sharpened from the point 138 to the outer surface 125 in order that cutting may accompany the full dilation required for the diameter of the shaft 116. Further grinding of the shaft 114 can form a radial shoulder 149 at the distal end of the outer walls 127–132.

This configuration of the shaft 114 is of further advantage due to its formation of interior passages or lumens 161, 163 and 165 which extend between the inner walls 117–119 and the outer walls 127–132. For example, the lumen 165 is defined by a surface 167 of the inner wall 117, a surface 170 of the inner wall 119, and an inner surface 172 of the outer wall 132.

Collectively the three lumens 161–165 form passages which extend along the shaft 116. These passages are well suited to receive an interior shield 176 of the type illustrated in FIG. 9. It is the purpose of this shield 176 to move from the retracted position wherein the cutting edges 141–145 are exposed, to a safety position wherein the cutting edges 141–145 are covered by the shield 176. The retracted position of the shield 176 exposes the sharpened tip 43 and therefore is preferred when the abdominal wall 16 is being penetrated. However, when the cutting tip 136 clears the wall 16, the advanced position of the shield 176 is preferred in order to prevent cutting of any interior organs. These respective retracted and advanced positions will be discussed in greater detail below.

Figure 9:
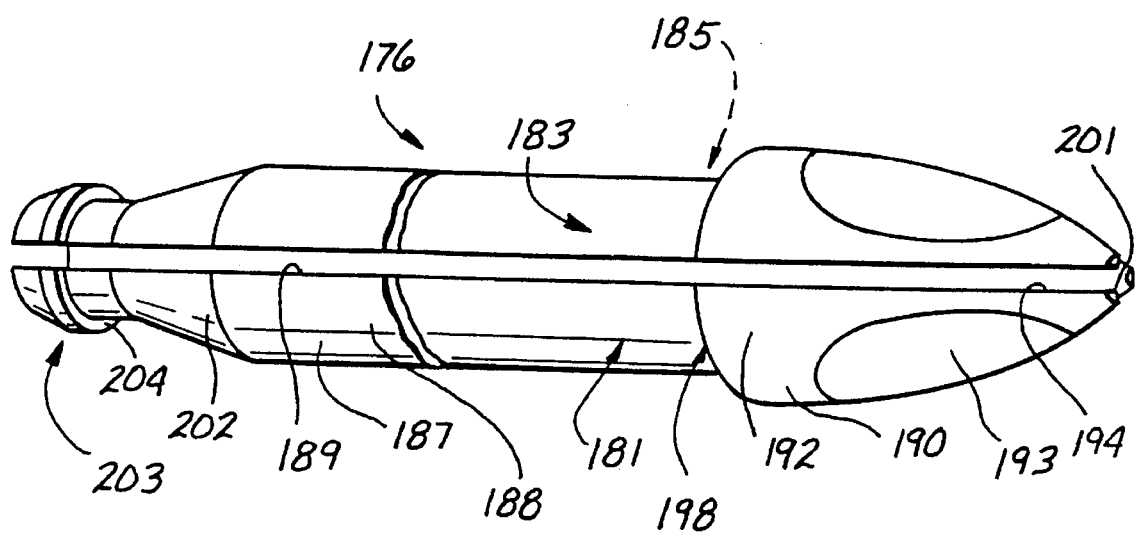

A preferred embodiment of the shield 176 is illustrated in FIG. 9 to include three separate shield elements 181, 183 and 185 which in a preferred embodiment have the same configuration but are associated with a different one of the lumens 161–165. By way of example, the shield section 181 includes an elongate rod 187 having an outer surface 188 and a pair of inner surfaces 189, 191 best illustrated in FIG. 8. The rod 187 is axially movable within the lumen 165 and extends distally to an enlarged protector 190 having an outer surface 192 and a pair of inner surfaces 194 and 196 also shown in FIG. 9. A shoulder 198 is formed where the diameter of the outer surface 188 of the rod 187 increases to the diameter of the surface 192 associated with the protector 190.

When operatively disposed, the inner surfaces 189 and 194 associated with the rod 187 and the protector 194, are in sliding engagement with the surface 167 associated with the inner wall 117. The outer surface 188 of the rod 187 slidably engages the inner surface 172 associated with the outer wall 132. Similarly, the surfaces 191 and 196 are in sliding engagement with the surface 170 of the inner wall 119.

In an axial direction, the surface 192 of the protector 190 curves radially inwardly with progressive distal positions so that it intersects the surface 194 along a line that is generally parallel to the curvature of the adjacent cutting edge 141. With this inward curvature, the surface 192 would intersect the surfaces 194 and 196 at a distal most point, were it not for this point being blunted by a radially flat surface 201.

At the proximal end of the shield element 181, the outer surface 188 is radially reduced along a taper 202 to form a flange 203 having a distally facing radial shoulder 204.

The working relationship between the inner walls 117–119, the associated passages or lumens 161, 165, and the shield elements 181, 185 is of particular interest to the present invention. In order for the shield elements 181–185 to properly cover the cutting edges 141–145 in the advanced position, it is desirable that the elements 181–185 be maintained in close proximity but sliding engagement with the surfaces of the inner walls 117–119. In the embodiment of FIG. 8, this is one of the functions associated with the outer walls 127–132. Thus the outer walls 127–132 limit the outward movement of the shield elements 181–185 so that these elements are maintained in close proximity and sliding engagement with the surfaces of the inner walls 117–119.

Figure 12:
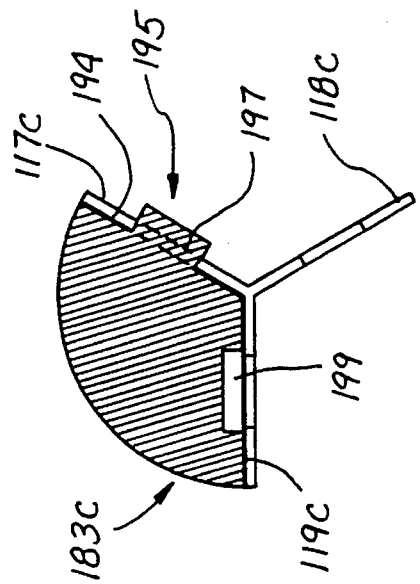
FIG. 12 is a radial cross section view similar to FIG. 10 of still a further embodiment of the wall and shield structure of the present invention.
Figure 11:
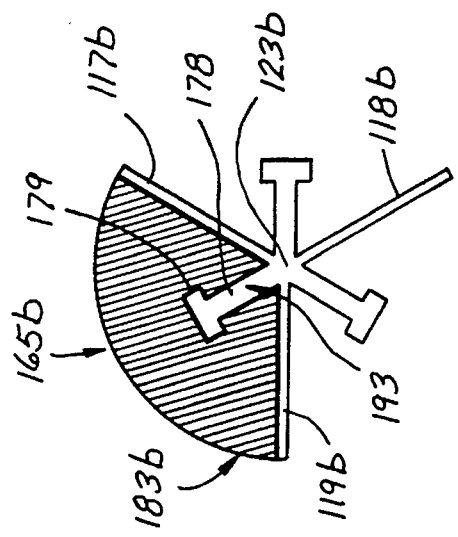
Figure 10:
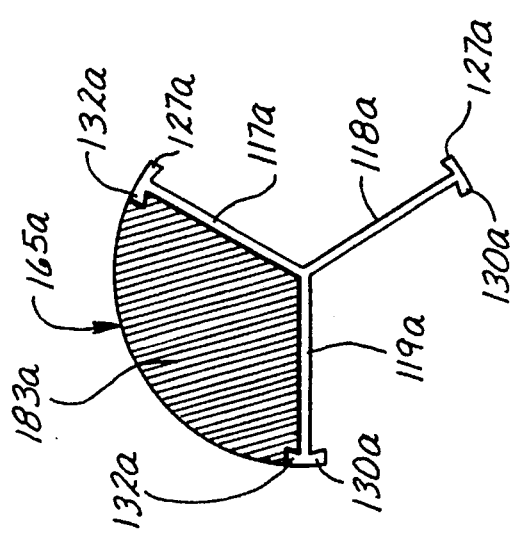

This function is served by other structural elements in the embodiments illustrated in FIGS. 10, 11 and 12 wherein similar elements are designated by the same reference numerals followed respectively by the lower case letters "a", "b" and "c". For example, in FIG. 10, the inner walls are designated by the reference numerals 117a, 118a, and 119a.

The embodiment of FIG. 10 differs from that of FIG. 8 in that the outer walls 127–132 are substantially removed except in the vicinity of the inner walls 117a–119a. Thus in FIG. 10, portions of the outer walls 130a and 132a remain in proximity to the inner wall 119a. In axial cross section, this integral relationship between the walls 130a, 132a and 119a have the configuration of the letter "T". A similar "T" configuration is formed by the walls 132a, 127a and 117a, and also the walls 127a, 130a and 118a.

In the FIG. 10 embodiment, the outer walls 127a–132a, although significantly foreshortened, still function to maintain the shield elements, such as the element 183a in proximity to and in sliding engagement with the associated inner walls, such as the inner walls 117a and 119a.

In the embodiment of FIG. 11, the outer walls are totally removed and the structure for retaining the shield element 183b includes a radial flange 178 and a transverse flange 179. The flange 178 extends radially outwardly from the axis 123b while the flange 179 extends generally transverse, such as perpendicular, to the radial flange 178. The resulting structure which has the configuration of the letter "T" functions as a key which registers with a similarly shaped keyway in the associated shield element 183b. In the illustrated embodiment, the key formed by the flanges 178, 179 is disposed angularly equidistant from the adjacent inner walls 117b and 119b so that the associated keyway 193 is centrally located within the associated shield element 183b. Similar keys and keyways can be formed for the other shield elements. This system of keys and keyways functions to maintain the shield elements 181b–185b in close proximity to and in sliding engagement with the associated inner walls 119b–123b.

In the embodiment of FIG. 12, the keys and keyways are reversed. Thus, a key 195 is formed on the shield element 183c and extends from the surface 194c and through a keyway 197 in the adjacent inner wall 117c. Since the key 195 extends through the inner wall 117c in this embodiment, a recess is formed in the adjacent shield element. For purposes of clarity, this element 185 is not shown in FIG. 12, but a similar recess 199 is illustrated for the shield element 183c. Once again, the keys, such as the key 195, and associated keyways, such as the keyway 197, in this embodiment function to maintain the associated shield elements, such as the shield element 183c, in close proximity to and in sliding engagement with the inner walls, such as the inner walls 119c and 117c.

In a preferred method of manufacture, the proximal end of the shaft 114 is drilled as illustrated in FIG. 13 to form an axial bore 206. This is typically accomplished using a drill 205 with a diameter equal to approximately the inside diameter of the outer walls 127–132. This effectively eliminates the inner walls 117–119 over the depth of the bore 206 which in a preferred embodiment is approximately ¾ inch. At this depth, the inner walls 117–119 form a radial shoulder 207. Proximally of the shoulder 207, the outer walls 127–132 provide the shaft 116 with a cylindrical configuration.

Further manufacturing steps are applicable to each of the embodiments of FIGS. 8 and 10–12. Initially, the shield elements 181–185 are individually inserted into the associated passages or lumens 161–165 of the shaft 116. This insertion continues until the shoulders, such as the shoulder 198 of the protector 190, abuts the distal radial shoulder 149 of the shaft 114. With this orientation, the rods (such as the rod 187) associated with the shield elements 181–185, are sufficiently long that their proximal flanges (such as the flange 203) extend beyond the shoulder 207 and into the axial bore 206.

Figure 15:
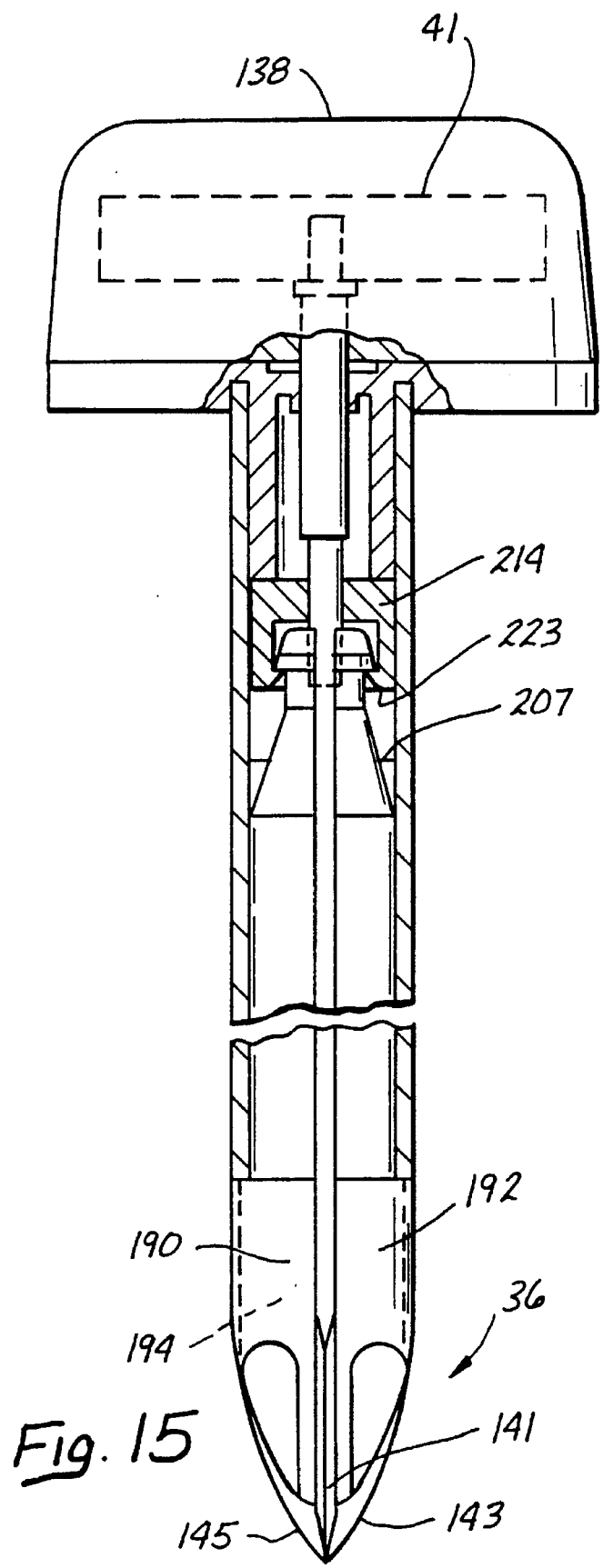
FIG. 15 is a side elevation view similar to FIG. 14 but illustrating the shield assembly in a retracted position.

At this point, a collar 214 is provided as best illustrated in FIG. 15. This collar 214 has generally cylindrical configuration with a side wall 216 extending between a proximal end wall 221 and a distal end wall 223. The proximal end wall 221 is drilled and threaded to form an axial hole 225, while the distal end wall 223 is formed as an annular flange 224 which extends inwardly from the distal end of the side wall 216 to form a distally facing shoulder 227.

The side wall 216 of the collar 214 is sized for disposition within the axial bore 206. Moving the collar 214 distally within the bore 206 causes the flanges 203 associated with the shield elements 181–185 to pass through the annular flange 224 of the distal end wall 223. Within the collar 214, the proximal ends of the shield elements 181–185 can be radially spread to lock the proximal end of the elements 181–185 into the collar 214. In this locked position, the shoulders 204 of the flanges 203 abut the shoulder 227 of the flange 224. This locking relationship maintains the shield elements 181–185 within the lumens 161–165 but permits a sliding axial movement which is accompanied by movement of the collar 214 within the axial bore 206.

This sliding axial movement is accommodated between a retracted position best illustrated in FIG. 15 wherein the distal end wall 223 associated with the collar 214 is spaced from the shoulder 207 at the distal end of the axial bore 206. At the distal end 36 of the obturator 14, this retracted position is associated with the protectors 190–194, being proximally spaced from the cutting edges 141–145. This exposes the cutting edges 141–145 thereby facilitating the cutting and penetration of the abdominal wall 16 by the trocar 10.

Figure 14:
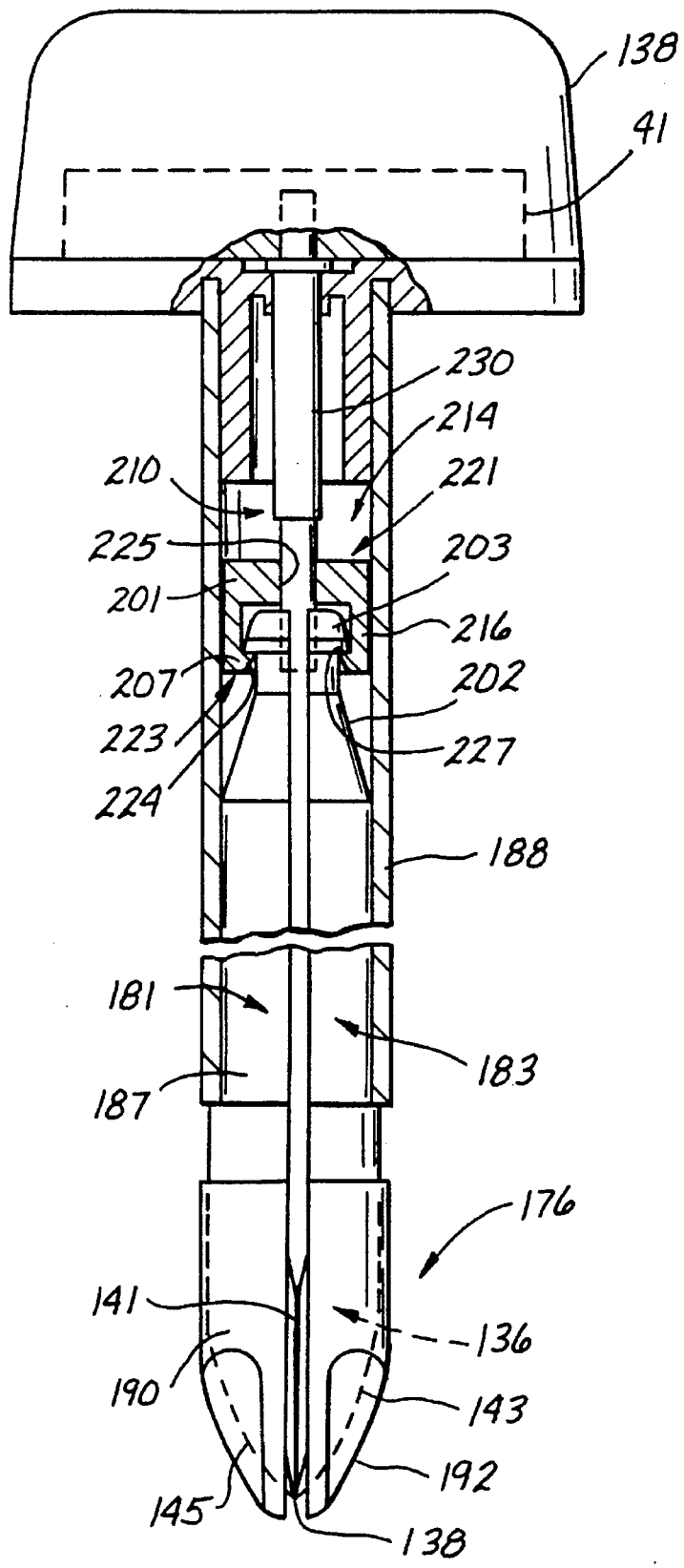
FIG. 14 is a side elevation illustrating the attachment of a retraction mechanism at the proximal end of the shaft and the mounting of the shield assembly into the distal end of the shaft, with the shield assembly illustrated in an advanced position.

The advanced position of the shield 176 is associated with an abutting relationship between the end wall 223 of the collar 214 and the shoulder 207 defining the axial bore 206. This advanced position is best illustrated in FIG. 14 where the protectors, such as the protector 190, are disposed distally of the point 138 to cover the cutting edges 141–145. This forward, advanced position of the shield 176 prevents further cutting by the tip 136.

It is of particular advantage that the distance separating the retracted position of FIG. 15 and the advanced position of FIG. 14 is relatively short in length. When this distance is reduced, the time required to move the shield 176 to the advanced position is shorter in duration. As a result, cutting can occur up to the point of full penetration of the abdominal wall 16 and then in a very short period of time, the shield 176 can be advanced to prevent further cutting. This short period of transition between the cutting and shielded modes of operation adds significantly to the protection of organs disposed interiorly of the abdominal wall 16.

With this construction, the retracted position of the shield 176 must be sufficiently proximal of the tip 136 to facilitate cutting of the abdominal wall 16. In the advanced position, the shield 176 must be sufficiently distal of the tip 136 to inhibit further cutting. In a preferred embodiment, the distance separating these advanced and retracted positions is equal to about the axial length of the bevels 147–154 associated with the respective cutting edges 141–145.

A minimal distance between the retracted position and the advanced position also facilitates use of a retraction mechanism such as that designated by the reference numeral 41 in FIG. 1. This mechanism 41 is preferably disposed within the handle 38 and can be of the type disclosed in applicant's copending application Ser. No. 08/045,369 filed Apr. 9, 1993 and entitled Surgical Trocar with Cutoff Circuit. This mechanism 41 includes a shaft 230 which is axially movable a distance at least as long as that separating the advanced position from the retracted position.

In a preferred embodiment, the distal end of the shaft 230 is sized and threaded for insertion through the threaded hole 225 of the collar 214. If the shaft 230 is made sufficiently long, its distal end can extend entirely through the end wall 221 to engage the flanges 203 associated with the shield sections 181–185. As the shaft 230 is screwed through the threaded hole 225, it spreads the flanges 203 radially outwardly to lock the proximal ends of the shield sections 181–185 into the collar 214. Thus, in accordance with the preferred method, screwing the shaft 230 into the collar 214 performs three functions. First, it locks the shield sections 181–185 to the collar 214; second, it attaches the shaft 230 to the shield 176; and third, it attaches the shaft 230 to the retraction mechanism 41 to facilitate axial movement of the shield 176 between the advanced and retracted positions.

As previously noted, the force of entry is dependent on both cutting and dilation forces. It has been found that if the surface 192 is provided with a dimple 193, one or the other of these forces may be accentuated. If the dimple 193 is provided with a concave configuration as illustrated in FIG. 9, the dilation required along the length of the dimple 193 is reduced. Accordingly, the cutting forces are accentuated along this region.

There are many features associated with the present invention which can be embodied in forms other than those illustrated and described. It will be apparent, for example that the cutting tip 136 can be formed with any plurality of blades each extending from the axis 32 outwardly to a cutting edge. For example, two blades equally spaced around 360° would form a single straight cutting edge in radial cross-section. Four blades could also be used typically requiring an associated number of the shield elements, such as the elements 181–185. Of course, the specific curvatures associated with the cutting edges 141–145 can also be varied along with the configuration of the surface 192 associated with the protectors 190. By varying the arcuate configuration of the cutting edges 141–145, as well as the configuration of the surface 192, with or without the dimples 193, can enable one to maintain a substantially constant force of entry.

Means other than the collar 214 can be used to engage and lock the proximal ends of the shield sections 181–185 and to provide for common movement with the shield 176.

Given the wide variations possible for embodying this concept, one is cautioned not to rely solely on the foregoing description and illustration of preferred embodiments. Rather, one is encouraged to determine the scope of the invention only with reference to the following claims.

We claim:

1. An obturator adapted for use in penetrating a body wall of a patient, including:

an elongate tube having a wall with an outer surface, an inner surface, and an axis extending between a proximal end and a distal end;

a handle disposed at the proximal end of the elongate tube;

a cutting section included in the cutting tip;

a mounting section included in the cutting tip, the mounting section being disposed proximally of the cutting section; and at least two mounting members included in the mounting section of the tip each extending outwardly of the axis of the tube to frictionally engage the inner surface of the tube at least one of the mounting members extending outwardly of the axis of the tube to an outer edge; and means disposed at the outer edge of the at least one mounting member for enhancing the frictional relationship between the at least one mounting member and the inner surface of the elongate tube, said means including a multiplicity of serrations each forming a point extending distally of the tube for engaging the wall of the tube and facilitating insertion of the tip into the tube while inhibiting removal of the tip from the tube.

2. The obturator recited in claim 1 wherein at least one of the two mounting members extends radially outwardly of the axis of the tube between the axis of the tube and the inner surface of the tube.

3. The obturator recited in claim 1 further comprising:

a least two blades included in the cutting section, each blade extending in a generally planar relationship with an associated one of the mounting members of the mounting section.

4. An obturator, comprising:

a longitudinal wall structure having an axis extending between a distal end and a proximal end, and at least one wall extending from the axis outwardly to a particular radius, the wall defining at least one longitudinal passage along the wall structure;

a cutting edge formed on the wall at the distal end of the wall structure, the cutting edge, extending between the axis and the particular radius of the wall;

at least one shield disposed in the passage and slidable axially along the passage in close proximity to the wall and between a retracted position wherein the cutting edge is sufficiently exposed to facilitate cutting and an advanced position wherein the cutting edge is sufficiently covered to inhibit cutting; and means having a fixed relationship with the wall structure for maintaining the shield in close proximity to the at least one wall, the maintaining means being disposed a distance from the axis which is not greater than the particular axis of the wall, and including portions of the wall defining an axial keyway, and a key extending from the shield into the keyway of the wall to permit axial movement of the key within the keyway while maintaining the shield in sliding engagement with the wall.

5. An obturator adapted for use in penetrating a body wall of a patient, including:

an elongate shaft having an axis extending between a proximal end and a distal end, and an outer wall including an outer surface defining a maximum outer diameter of the shaft, and an inner surface defining a maximum inner diameter of the shaft;

a tip section disposed at the distal end of the elongate shaft;

a plurality of inner walls included in the tip section and extending distally of the shaft, the walls being angularly spaced around the axis of the shaft;

the inner walls of the tip section extending to engage the outer wall of the shaft and to form with the outer wall a plurality of passages extending at least partially along the shaft;

at least one of the inner walls being defined by an inclined cutting edge extending along a line from the axis of the shaft to the outer surface of the shaft;

at least one shield disposed in an associated one of the passages of the shaft, the shield including a rod portion extending from a proximal end to a distal end and having an outer surface slidably engaging the inner surface of the outer wall of the shaft, and an enlarged protector portion secured to the distal end of the rod, the enlarged protector portion having an outer surface defining a maximum outer diameter of the protector portion which is larger than the maximum inner diameter of the shaft; and the shield being slidable axially between a retracted position wherein the cutting edge is exposed to facilitate cutting of the body wall and an extended position wherein the cutting edge is covered by the protector portion of the shield to inhibit cutting.

6. The obturator recited in claim 5 further comprising means for locking the shield in the extended position.

7. The obturator recited in claim 5, wherein at least one of the inner walls of the tip section includes a bevel extending along the entire inclined edge between the axis of the shaft and the outer surface of the shaft to provide the inclined edge with a sharp configuration, the bevel having a radial length and a maximum axial length.

8. The obturator recited in claim 7, wherein the extended position of the shield is axially spaced from the retracted position by a distance not greater than about the maximum axial length of the bevel.

9. The obturator recited in claim 5 wherein the outer wall and the inner wall in radial cross section generally form a "T".

10. The obturator recited in claim 5 wherein the wall structure further comprises:

a first inner wall and a second inner wall;

a first outer wall extending transverse to the first inner wall;

a second outer wall extending transverse to the second inner wall; and the first outer wall and the second outer wall forming a continuous surface between the first inner wall and the second inner wall.

11. An obturator adapted for use in penetrating a body wall of a patient, including:

an elongate shaft having an axis extending between a proximal end and a distal end, and an outer wall including an outer surface defining a maximum outer diameter of the shaft, and an inner surface defining a maximum inner diameter of the shaft;

a tip section disposed at the distal end of the elongate shaft;

a plurality of inner walls included in the tip section and extending distally of the shaft, the walls being angularly spaced around the axis of the shaft;

the inner walls of the tip section extending to engage the outer wall of the shaft and to form with the outer wall a plurality of passages extending at least partially along the shaft;

a first one of the inner walls defined by a first inclined cutting edge extending along a line from the axis of the shaft to the outer surface of the shaft;

a second one of the inner walls defined by a second inclined cutting edge extending along a line from the axis of the shaft to the outer surface of the shaft;

a first imaginary plane extending between the axis of the shaft and the first cutting edge;

a second imaginary plane extending through at least a first point on the first cutting edge and a second point on the second cutting edge;

the second imaginary plane forming a facet angle with the first imaginary plane at the first point;

a bevel disposed along the first cutting edge and forming a bevel angle with the first imaginary plane at the first point;

the bevel angle being less than the facet angle to sharpen the first cutting edge;

at least one shield disposed in an associated one of the passages of the shaft, the shield including a rod portion having an outer surface slidably engaging the inner surface of the outer wall of the shaft, and an enlarged protector portion and having an outer surface defining a maximum outer diameter of the protector portion which is larger than the maximum inner diameter of the shaft; and the shield being slidable axially between a retracted position wherein the cutting edge is exposed to facilitate cutting of the body wall and an extended position wherein the cutting edge is covered by the protector portion of the shield to inhibit cutting.

12. The obturator recited in claim 11 wherein the first cutting edge has a straight configuration.

13. The obturator recited in claim 11 wherein the first cutting edge has the configuration of an arc and the second imaginary plane is tangential to the arc at the first point.

* * * * *